United States Patent [19]
Petronella et al.

[11] Patent Number: 4,720,352
[45] Date of Patent: Jan. 19, 1988

[54] PROCESS FOR THE PREPARATION OF VANADIUM-CONTAINING MIXED METAL SOAP SOLUTIONS

[75] Inventors: Joseph Petronella, Old Bridge Township, Middlesex County; Samuel J. Bellettiere, South Brunswick, both of N.J.

[73] Assignee: Nuodex Inc., Piscataway, N.J.

[21] Appl. No.: 793,870

[22] Filed: Nov. 1, 1985

[51] Int. Cl.⁴ .................. B01J 13/00; C10M 113/08; C10M 155/00
[52] U.S. Cl. ........................................ 252/308; 252/1; 252/35; 252/37.7; 252/39; 252/49.5; 252/49.7; 260/414; 106/310
[58] Field of Search .............. 525/16; 562/549; 252/1, 252/315.4, 308, 35, 37.7, 39, 49.5, 49.7; 106/310; 260/414

[56] References Cited

U.S. PATENT DOCUMENTS

| | | | |
|---|---|---|---|
| 2,095,508 | 10/1937 | Meider | 106/310 |
| 2,417,429 | 3/1947 | McLennan | 252/36 |
| 2,584,041 | 1/1952 | Nowak et al. | 260/414 |
| 3,362,972 | 1/1968 | Wallington | 260/414 |
| 3,483,250 | 12/1969 | Sugarman | 562/549 |
| 3,660,288 | 5/1972 | Hansen | 252/39 X |
| 3,914,336 | 10/1975 | Baker | 525/16 |
| 4,083,890 | 4/1978 | Drake et al. | 525/16 |
| 4,162,986 | 7/1979 | Alkaitis et al. | 252/37.7 X |
| 4,633,001 | 12/1986 | Cells | 556/44 |

Primary Examiner—John F. Terapane
Assistant Examiner—Catherine S. Kilby
Attorney, Agent, or Firm—James P. Scullin

[57] ABSTRACT

Solutions of complexed mixed soaps of vanadium and at least one other metal in organic solvents are produced by the reaction of an inorganic vanadium compound, an oxidizable metal, and an organic monocarboxylic acid, in the presence of oxygen, water, and an inert, water-immiscible organic solvent.

19 Claims, No Drawings

PROCESS FOR THE PREPARATION OF VANADIUM-CONTAINING MIXED METAL SOAP SOLUTIONS

BACKGROUND OF THE INVENTION

1. Field of the Invention

This invention pertains to the preparation of vanadium-containing mixed metal salt or soap complexes as solutions in organic solvents.

2. Description of the Prior Art

Solvent-soluble metal salts or soaps, including vanadium salts or soaps, have been shown to have utility as driers for paints, varnishes and printing inks, as lubricant additives, and as catalysts for chemical reactions. Stewart (*Official Digest*, June 1954. p. 413–25) described the high degree of activity of vanadium naphthenate as a paint drier. In U.S. Pat. No. 3,914,336, Baker disclosed curing accelerators for unsaturated polyester resins that comprise mixtures of stannous salts and vanadium salts. In U.S. Pat. No. 3,079,363, Koch et al disclosed the use of vanadium compounds, such as vanadium naphthenate, as promoters for the hydroperoxide catalysis of unsaturated polyester resins. In U.S. Pat. No. 3,483,250, Sugarman disclosed the utility of vanadium soaps, in combination with iron soaps or cobalt soaps, as catalysts for the oxidation of n-butane to produce acetic acid. In U.S. Pat. No. 3,526,645, Vangermain et al described a process for the epoxidation of olefins using a catalyst comprised of, for example, a mixture of vanadium naphthenate and an octoate or naphthenate of cobalt, nickel, or manganese.

In U.S. Pat. No. 2,095,508, Meidert disclosed a process for preparing metal naphthenates, including vanadium naphthenate, by a double-decomposition reaction between aqueous solutions of salts of the desired metal and aqueous solutions of alkali metal naphthenates, in the absence of volatile organic solvents. In U.S. Pat. No. 3,362,972, Kollar described a process for making vanadium salts by reacting $V_2O_5$ with oxalic acid to form vanadium oxalate, followed by replacement of the oxalate group by a monocarboxylic acid. In U.S. Pat. No. 2,417,429, McLennan disclosed a process for preparing lubricating greases that comprises the formation of complex basic soaps in which at least two metals are present by saponification in mineral oil, in the presence of oxygen and at temperatures of at least 400° F. One of the metals may be vanadium.

In U.S. Pat. No. 2,890,232, Rogers et al disclosed a method of making soaps of metals of Group II of the periodic table that comprises reacting metal oxides or hydroxides with higher fatty acids in the presence of 0.5–3.0 mols of water per mol of metal compound. In U.S. Pat. No. 2,584,041, Nowak et al disclosed a process for the preparation of oil-soluble metal soaps by the reaction of organic acids with finely-divided metals in the presence of water, and alternatively in the presence of air. The metals that can be used in this process include aluminum, strontium, lead, cobalt, manganese, iron, copper, zinc, and nickel.

BRIEF SUMMARY OF THE INVENTION

Although there are many known industrial uses of vanadium soaps, full development of the potential of such uses has been hampered by the lack of availability of vanadium soap solutions of acceptably low viscosity, clarity, stability, and cost. The preparation of vanadium carboxylates by processes known in the prior art has been difficult and expensive, frequently requiring high temperatures and relatively costly raw materials. The double decomposition process requires high cost ingredients, and produces a large quantity of waste water that must be treated to make it environmentally-acceptable prior to disposal. In addition it is difficult, or impossible, to completely free the product from all traces of alkali metal salt. Such contamination often has an adverse effect on the utility of the vanadium soap as a drier or catalyst. The process that comprises fusion of a vanadium oxide with oxalic acid followed by replacement with a higher carboxylic acid has high raw material cost, and also requires the use of large amounts of water during the reaction, in the order of 20–30% of the batch weight, which must be removed and then treated in order to be safely discarded.

The present invention provides an economical process for preparing solutions of vanadium salts in organic solvents, in the form of a complex with salts of at least one other metal. The salts of this invention are those of monocarboxylic acids having from 1 to 18 carbon atoms, naphthenic acids, and tall oil fatty acids, and are commonly referred to in the art as soaps. The process herein disclosed overcomes the disadvantages of prior art processes for making vanadium soaps: commercial grades of raw materials can be used; there is essentially no waste water problem to be dealt with since very little water is either added to, or produced by, the reaction; neither long reaction times nor very high reaction temperatures are required; and there are no inorganic salt by-products to be washed out, or to contaminate the soap solutions. Generally, only a simple filtration is needed to clarify the product and remove any traces of unreacted starting materials. The process of this invention provides solutions having higher total metal content than is usually attainable using processes of the prior art. Fluid, clear, products with high metal contents are feasible when this method is used.

The objectives of this invention are achieved by co-reacting a mixture comprising an inorganic vanadium compound, an oxidizable metal in comminuted form, and an organic carboxylic acid, in the presence of water, oxygen, and an organic solvent. If desired, in order to aid the package-stability of the final product, a minor amount of a hydroxyl-containing compound can also be present in the reaction mixture, or it can be added after the reaction is completed. The vanadium-containing complexed mixed metal soap solutions can be used as driers for paints, varnishes and printing inks, lubricant additives, fuel oil additives, accelerators for the curing of polyester resins, catalysts for chemical reactions, and in many other applications for which metal soaps are commonly employed.

DETAILED DESCRIPTION OF THE INVENTION

As a source of vanadium for use in this process, the oxides, chlorides, oxychlorides and sulfates of vanadium are suitable, as well as ammonium and alkali metal vanadates and vanadic acids. We prefer to use vanadium pentoxide or ammonium metavanadate. Although we prefer to use a single vanadium compound, mixtures of two or more can be used if desired, without departing from the scope of the invention.

As the oxidizable metal we can use aluminum, strontium, copper, zinc, iron, cadmium, zirconium, bismuth, lead, manganese, antimony, tin, cobalt, or nickel. A single metal can be used, or a mixture of two or more. As will be understood by those skilled in the art, the choice of metal, or metals, used will depend on the intended use of the vanadium/metal soap complex solution. By way of example, if the product is to be used as a paint drier a vanadium/cobalt, vanadium/iron, or vanadium/cobalt/manganese mixed soap will be useful; and for use as an accelerator for unsaturated polyester resins a vanadium/tin or vanadium/cobalt mixed soap may be desired. Although these vanadium-containing complexed mixed soaps are frequently useful by themselves, for some applications we have found it advantageous to use them in admixture with a soap of another metal. By way of example, when a vanadium/cobalt metal soap complex is employed as an accelerator for unsaturated polyester resins or as a drier for water-soluble alkyd paint composition, the addition of a potassium salt or soap to the complex results in improved stability of the polyester resin or paint composition. In order to be used in this reaction, the oxidizable metal must be in comminuted, or finely-divided, form.

As the soap-forming acid, we use straight-chain or branched, saturated or unsaturated, organic monocarboxylic acids having from 1 to 18 carbon atoms, naphthenic acids, tall oil fatty acids or mixtures thereof. Examples of suitable acids include: formic, acetic, propionic, n-butyric, iso-butyric, n-pentanoic, 2-methylbutanoic, 3-methylbutanoic, neopentanoic, n-hexanoic, 2-ethylbutanoic, neohexanoic, n-heptanoic, 5-methylhexanoic, neoheptanoic, n-octanoic, 6-methylheptanoic, 2,5-dimethylhexanoic, 2-ethylhexanoic, 2-ethyl-4-methylpentanoic, neooctanoic, n-nonanoic, neononanoic, 7-methyloctanoic, 2-methylnonanoic, n-decanoic, 2-ethyloctanoic, neodecanoic, 8-methylnonanoic, undecanoic, dodecanoic, tetradecanoic, octadecanoic, 10-undecenoic, 2-ethyl-3-propylacrylic, octenoic, and oleic acids. We prefer to use branched-chain saturated monocarboxylic acids having 3 to 13 carbon atoms, and particularly prefer to use 2-ethylhexanoic acid and naphthenic acids.

The organic solvent used as a component of the reaction mixture, and as a diluent for the finished product, is an inert, water-immiscible solvent, preferable an aliphatic or aromatic hydrocarbon or mixture thereof. Suitable solvents include such hydrocarbons as benzene, toluene, xylene, ethylbenzene, dipentene, turpentine, petroleum hydrocarbon fractions such as gasoline, kerosene, mineral spirits, diesel fuel and naphtha, and such chlorinated hydrocarbons as carbon tetrachloride, O-dichlorobenzene, monochlorotoluene, ethylene dichloride and perchlorethylene. A preferred solvent is mineral spirits. Mixtures of two or more of any of these solvents can be used, if desired. Oxygenated solvents can also be used if desired, without departing from the scope of the invention.

Alternatively, although not generally required, a stabilizer, or peptizer, can be used in the process of this invention. As a stabilizer we use hydroxy-containing compounds such as alkanols containing from 1 to 10 carbon atoms, glycols having from 2 to 9 carbon atoms, glycol monoethers having from 3 to 14 carbon atoms such as the mono-methyl, -ethyl, -butyl, -hexyl, or -octyl ethers of ethylene glycol, diethylene glycol, propylene glycol or dipropylene glycol and mixtures thereof. The stabilizers may enhance the package stability of the final product, and also may reduce its viscosity. The stabilizer can be present in the reaction mixture, where it has little or no effect on the course or rate of the reaction, or it can be added to the product after reaction is complete. Only a small quantity of stabilizer is used, and the exact amount is not critical. We have found that quantities ranging from about 5% to about 15% by weight based on the total weight of all of the other ingredients give satisfactory results.

The ratio of vanadium compound to oxidizable metal or metals is not critical and can be varied over a wide range, depending on the ratio of vanadium to other metal or metals that is desired in the final product.

Equivalent amounts of the total of the vanadium compound and the oxidizable metal and the monocarboxylic acid, or a stoichiometric excess of either acid or vanadium compound and metal, can be used in this process. It is generally preferred to use a molar excess of from about 0.1% to about 50% for the monocarboxylic acid.

The amount of water added to the reaction mixture is not critical, and can range from about 20% to about 120% by weight based on the weight of the oxidizable metal. Preferably, the amount of water ranges from about 50% to about 100% by weight based on the weight of the oxidizable metal.

The reaction is carried out in the presence of oxygen, preferably by sparging the reaction mixture with an oxygen-containing gas while maintaining the reaction mixture at an elevated temperature. The preferred oxygen-containing gas is air. Oxygen can also be added to the reaction mixture as a compound, such as a peroxide, if desired. The amount of oxygen that is added is not critical, and can be varied within wide limits. In most cases, air is sparged through the reaction mixture at such a rate that a total of from about 2 moles to 100 moles of oxygen is provided per mole of oxidizable metal.

The amount of water-immiscible organic solvent is not critical, and can be varied over a wide range. The solvent does not take part in the reaction, but serves mainly to provide a fluid medium for the reactants and to enhance intimate contact there among. Those skilled in the art will understand that too much solvent will be detrimental to the rate of reaction and may also result in too dilute a final product; and that too little may result in too viscous a reaction mixture as the mixed soap product is formed. Amounts of solvent ranging from about 10% to about 150% by-weight based on the total weight of all other components of the reaction mixture have given satisfactory results.

The average particle size of the oxidizable metal is not critical, but as will be obvious to those skilled in the art it is desirable that the metal be finely divided in order that a large surface area per unit weight be exposed to the other reactants in order to increase the rate of reaction. Although the oxidizable metal can be in the form of granules, chips, shavings, or wire without departing from the scope of the invention, it is preferred that the metal be in powdered, or comminuted form. Satisfactory results have been obtained with comminuted metals having a particle size such that 100% passes through a 100 mesh screen.

In order to carry out the reaction, the vanadium compound, oxidizable metal, monocarboxylic acid, water, and solvent are comingled in a suitable reaction vessel, the mixture is agitated and its temperature is elevated; and the mixture is continuously sparged with an oxygen-containing gas. The elevated temperature and sparging are maintained until substantially no unreacted vanadium compound or oxidizable metal remains in the reaction mixture, or until the acid number of the reaction mixture has reached the desired level. When the reaction has been completed, the reaction mixture is heated, preferably under vacuum, to remove water from it, and filtered, if necessary, to remove any insoluble materials that it may contain. The degree of vacuum is not critical. We have found that a pressure of about 100 mm of mercury is satisfactory.

The product, which is a solution of a soap of vanadium complexed with at least one other metal of an organic monocarboxylic acid in an inert, water-immisible, organic solvent, contains from about 5% to about 25% by weight of the total of vanadium and other metal or metals. It can be used without purification or further treatment, other than the adjustment of the metal content by dilution with additional organic solvent if desired, in any of the applications in which such mixed-metal soap solutions are commonly used.

We believe that during the course of the reaction there is an oxidation-reduction reaction occurring between the metal powder (oxidizing) and the inorganic vanadium compound (reducing) which results in the formation of a complexed mixed soap that is not obtained when separately prepared vanadium soap solutions and other metal soap solutions are simply mixed together. However, we are not bound by this theory, and it is not to be considered as limiting the scope of this invention.

The process described herein can be carried out under atmospheric pressure, subatmospheric pressures, or superatmospheric pressures. Although the rate of reaction is increased under superatmospheric pressure, it is usually more economical and more convenient to use atmospheric pressure, and that is the preferred method. Reaction temperatures within the range of from about 60° C. to about 150° C. can generally be used, and if desired even higher or lower temperatures can be used without departing from the scope of the invention. Optimum results have been obtained when the reaction was carried out at temperatures in the range of 70° C. to 95° C. at atmospheric pressure. It will be obvious to those skilled in the art that the optimum temperature for any given reaction mixture will depend at least in part on the particular vanadium compound, metal or metals, and carboxylic acid or acids being used. The temperature used for the final step of removal of water is not critical, and can be varied over a wide range. We have found a temperature of about 135° C. to be satisfactory. The degree of vacuum employed is also not critical, the purpose of the vacuum being merely to increase the rate of water removal.

The following examples are only illustrative of the invention, and are not to be considered limitative of its scope.

EXAMPLE 1

Vanadium-Cobalt 2-ethylhexanoate

A mixture of 25.1 grams (0.424 mole) of cobalt powder (100% through 100 mesh screen), 9.0 grams (0.098 mole) vanadium pentoxide, 165.7 grams (1.143 moles) of 2-ethylhexanoic acid (acid number 387), 250 grams of mineral spirits and 25 grams of water was heated to 95° C. and, with air sparging of about 30 liters/hour, was at 95° C. for 8.5 hours. The reaction product was heated to 135° C. under vacuum to remove the water, filtered and diluted with mineral spirits to 5.2% cobalt and 1.0% vanadium.

The product was a transparent, fluid, solution containing 45.1% non-volatile material, and having a viscosity of 2 cs at 25° C. and an acid number of 37. The yield, based on the total of vanadium and cobalt charged, was 90%.

COMPARATIVE EXAMPLE A

Vanadium 2-ethylhexanoate

A mixture of 21.5 grams (0.236 mole) of vanadium pentoxide, 128.1 grams (0.884 mole) of 2-ethylhexanoic acid (acid number 387) and 100 grams of mineral spirits was heated to 95° C. for 4.5 hours with no reaction occurring.

This comparative example shows the lack of reactivity of vanadium pentoxide with 2-ethylhexanoic acid, in the absence of the other ingredients used in Example 1.

EXAMPLE 2

Vanadium-Cobalt 2-ethylhexanoate

A mixture of 25.1 grams (0.424 mole) of cobalt powder, 9.0 grams (0.098 mole) of vanadium pentoxide, 50 grams of hexylene glycol (stabilizer), 25 grams of water, 200 grams of mineral spirits and 165.7 grams (1.143 moles) of 2-ethylhexanoic acid (acid number 387 was heated to 95° C. and, with air sparging of 30 l/hr., held at 95° C. for 6.5 hours. The reaction product was heated to 135° C. under vacuum to remove water, filtered and diluted with mineral spirits to 5.6% cobalt and 1.8% vanadium.

The product was a transparent, fluid, solution containing 48.5% non-volatile material, and having a viscosity of 2 cs at 25° C. and an acid number of 31. A quantitative yield, based on the total of vanadium and cobalt charged, was obtained.

EXAMPLE 3

Vanadium-Cobalt 2-ethylhexanoate

A mixture of 25.1 grams (0.424 mole) of cobalt powder, 11.6 grams (0.098 mole) of ammonium metavanadate, 165.7 grams (1.143 moles) of 2-ethylhexanoic acid (acid number 387), 50 grams of hexylene glycol (stabilizer), 25 grams of water and 200 grams of mineral spirits was heated to 95° C. and, with air sparging of 30 l/hr., held at 95° C. for 9 hours. The reaction product was heated to 135° C. under vacuum to remove water, filtered and diluted with mineral spirits to 6.2% cobalt and 0.7% vanadium.

The product was a transparent, fluid solution containing 41.8% non-volatile material, and having a viscosity of 2 cs at 25° C. and an acid number of 55. The yield was 90% based on the total of vanadium and cobalt charged.

COMPARATIVE EXAMPLE B

Vanadium 2-ethylhexanoate

A mixture of 69.6 grams (0.589 mole) of ammonium metavanadate, 342.0 grams (2.356 moles) of 2-ethylhexanoate (acid number 387) and 130 grams of mineral spirits was heated to 95° C. and held for 1 hour without reaction occurring. The temperature was gradually increased to 195° C. in 3.5 hours while the water of reaction was removed. The reaction product solidified at room temperature.

EXAMPLE 4

Vanadium-Cobalt Naphthenate

A mixture of 9.0 grams (0.098 mole) of vanadium pentoxide, 25.1 grams (0.424 mole) of cobalt powder, 266.4 grams (1.045 moles) of naphthenic acid (acid number 220), 30 grams hexylene glycol (stabilizer), 25 grams of water and 150 grams of mineral spirits was heated to 95° C. and, with air sparging of 30 l/hr., held at 95° C. for 6 hours. The reaction product was heated to 135° C. under vacuum to remove water, filtered and diluted with mineral spirits to 4.5% cobalt and 1.0% vanadium.

The product was a transparent, fluid, solution containing 61.0% non-volatile material, and having a viscosity of 20 cs at 25° C. and an acid number of 33. The yield, based on the total of vanadium and cobalt charged, was 90%.

COMPARATIVE EXAMPLE C

Vanadium Naphthenate

A mixture of 34.5 grams (0.294 mole) of ammonium metavanadate, 309.5 grams (1.181 moles) of naphthenic acid (acid number 214) and 145 grams of mineral spirits was heated to 95° C. and held 1 hour without reaction occurring. The temperature was gradually increased to 195° C. in 2 hours while the water of reaction was removed. The reaction product was cooled to 120° C., 25 grams of hexylene glycol was added, and then filtered. The resulting solution contained 3.0% vanadium.

This example illustrates the high reaction temperature needed to produce a vanadium soap solution by a method of the prior art. Although the product was fluid, it was not transparent when cooled to room temperature, but was opaque. This shows that the vanadium soap was either incompletely soluble, or unstable. The product contained 66.1% non-volatile material and had a viscosity of 210 cs at 25° C. The yield was 96% based on the amount of vanadium charged.

EXAMPLE 5

Vanadium-Cobalt 2-ethylhexanoate

A mixture of 45.2 grams (0.764 mole) of cobalt powder, 27.0 grams (0.294 mole) of vanadium pentoxide, 306.8 grams (2.116 moles) of 2-ethylhexanoic acid (acid number 378), 30 grams of hexylene glycol (stabilizer), 25 grams of water and 100 grams of mineral spirits was heated to 95° C. and, with an air sparge of 30 l/hr., held at 95° C. for 10.5 hours. The reaction product was heated to 135° C. under vacuum to remove water, filtered and diluted with mineral spirits to 9.0% cobalt and 3.0% vanadium.

The product was a transparent, fluid, solution containing 76.1% non-volatile material, and having a viscosity of 25 cs at 25° C. and an acid number of 56. The yield was quantitative, based on the total of vanadium and cobalt charged.

EXAMPLE 6

Vanadium-iron 2-ethylhexanoate

A mixture of 18 grams (0.196 mole) of vanadium pentoxide, 51.1 grams (0.895 mole) of iron powder (97.8% iron), 348.2 grams (2.402 moles) of 2-ethylhexanoic acid (acid number 387), 30 grams of hexylene glycol (stabilizer), 25 grams of water and 60 grams of mineral spirits was agitated for 1 hour with an air sparge. The mixture was then heated to 70° C. and held for 11.5 hours. The reaction product was heated to 135° C. under vacuum to remove water, filtered and diluted with mineral spirits to 6.0% iron and 1.0% vanadium.

EXAMPLE 7

Vanadium-Cobalt Mixed Soap

A mixture of 45.2 grams (0.764 mole) of cobalt powder, 27.0 grams (0.294 mole) of vanadium pentoxide, 127.8 grams (0.882 mole) of 2-ethylhexanoic acid (acid number 378), 142.5 grams (0.887 mole) of mixed neoacids having from 9 to 13 carbon atoms (acid number 347), 67.0 grams (0.882 mole) of propionic acid, 60.0 grams of mineral spirits, 30.0 grams of dipropylene glycol monomethyl ether (stabilizer), and 25.0 grams of water was heated to 95° C. and, with an air sparge of 30 l/hr, was held at 95° C. for 10 hours. The reaction product was then heated to 135° C. under vacuum to remove water, and filtered.

The resulting clear solution contained 8.9% cobalt and 3.1% vanadium and had a non-volatile content of 85.6% and a viscosity of 1300 cs at 25° C.

The foregoing examples were prepared in a one-liter, 4-necked flask, flask equipped with agitator, thermometer, reflux condenser, and sampling tube, but any suitable reaction vessel can be used in carrying out this process.

EXAMPLES 8 through 19

Example 1 is repeated replacing the cobalt with an equivalent amount of powdered aluminum (Example 8), strontium (Example 9), copper (Example 10), zinc (Example 11), cadmium (Example 12), zirconium (Example 13), bismuth (Example 14), lead (Example 15), manganese (Example 16), antimony (Example 17), tin (Example 18), or nickel (Example 19). In each case a transparent solution of a complexed mixed soap of vanadium and other metal is obtained.

We claim:

1. A process for the preparation of a solution in an organic solvent of a complexed mixed soap of vanadium and at least one other metal which comprises comingling (a) at least one inorganic vanadium compound selected from the group consisting of vanadium oxides, vanadium chlorides, vanadium oxychlorides, vanadium sulfates, ammonium vanadates, alkali metal vanadates, and vanadic acids, (b) at least one comminuted metal selected from the group consisting of aluminum, strontium, copper, zinc, iron, cadmium, zirconium, bismuth, lead, manganese, antimony, tin, cobalt, and nickel, (c) at least one organic monocarboxylic acid selected from the group consisting of straight chain or branched chain saturated or unsaturated monocarboxylic acids having from 1 to 18 carbon atoms, naphthenic acids, and tall oil fatty acids, and mixtures thereof, in an amount to provide a stoichiometric excess of from about 0.1% to about 50% of said monocarboxylic acid over the total equivalents of said inorganic vanadium compound and said comminuted metal, (d) water, and (e) a water-immiscible inert organic solvent to form a reaction mass, and heating and agitating said reaction mass in the presence of oxygen until reaction is essentially complete.

2. The process of claim 1 wherein oxygen is introduced into said reaction mass by means of sparging with an oxygen-containing gas.

3. The process of claim 2 wherein said oxygen-containing gas is air.

4. The process of claim 1 wherein said inorganic vanadium compound is vanadium pentoxide.

5. The process of claim 1 wherein said vanadium compound is ammonium metavanadate.

6. The process of claim 1 wherein said metal is cobalt.

7. The process of claim 1 wherein said metal is iron.

8. The process of claim 1 wherein said organic monocarboxylic acid is a saturated, branched-chain monocarboxylic acid having from 3 to 13 carbon atoms.

9. The process of claim 8 wherein said organic monocarboxylic acid is 2-ethylhexanoic acid.

10. The process of claim 1 wherein said organic monocarboxylic acid is naphthenic acid.

11. The process of claim 1 wherein said water-immiscible organic solvent is mineral spirits.

12. The process of claim 1 wherein said reaction mass also comprises a stabilizer selected from the group consisting of alkanols having from 1 to 10 carbon atoms, glycols having from 2 to 9 carbon atoms, glycol monoethers having from 3 to 12 carbon atoms, and mixtures thereof.

13. The process of claim 12 wherein said stabilizer is hexylene glycol.

14. The process of claim 12 wherein said stabilizer is dipropylene glycol monomethyl ether.

15. A solution in an organic solvent of a complexed mixed soap of vanadium and at least one other metal, which is the product of a process comprising the reaction of at least one inorganic vanadium compound, at least one oxidizable metal, and at least one organic monocarboxylic acid, in the presence of water, oxygen, and an inert water-immiscible organic solvent; said vanadium compound being selected from the group consisting of vanadium oxides, vanadium chlorides, vanadium oxychlorides, vanadium sulfates, ammonium vanadates, alkali metal vanadates, and vanadic acids; said oxidizable metal being selected from the group consisting of an aluminum, strontium, copper, zinc, iron, cadmium, zirconium, bismuth, lead, manganese, antimony, tin, cobalt, and nickel; and said organic monocarboxylic acid being selected from the group consisting of straight chain or branched chain, saturated or unsaturated monocaboxylic acids having from 1 to 18 carbon atoms, naphthenic acids, tall oil fatty acids, and mixtures thereof, and being present in an amount to provide a stoichiometric excess of from about 0.1% to about 50% of said monocarboxylic acid over the total equivalents of said inorganic vanadium compound and said oxidizable metal.

16. A product according to claim 15 that is a solution of a complexed mixed soap of vanadium, cobalt, and 2-ethylhexanoic acid.

17. A product according to claim 15 that is a solution of a complexed mixed soap of vanadium, cobalt, and naphthenic acid.

18. A product according to claim 15 that is a solution of a complexed mixed soap of vanadium, iron, and 2-ethylhexanoic acid.

19. A product according to claim 15 that is a complexed mixed soap of vanadium, cobalt, 2-ethylhexanoic acid, propionic acid and mixed neo acids having from 9 to 13 carbon atoms.

* * * * *